US008232877B2

(12) United States Patent
Husain

(10) Patent No.: US 8,232,877 B2
(45) Date of Patent: Jul. 31, 2012

(54) NAVIGATION SYSTEM WITH CONTEXT BOUNDARY MONITORING MECHANISM AND METHOD OF OPERATION THEREOF

(75) Inventor: Aliasgar Mumtaz Husain, Milpitas, CA (US)

(73) Assignee: Telenav, Inc., Sunnyvale, CA (US)

( * ) Notice: Subject to any disclaimer, the term of this patent is extended or adjusted under 35 U.S.C. 154(b) by 516 days.

(21) Appl. No.: 12/609,347

(22) Filed: Oct. 30, 2009

(65) Prior Publication Data

US 2011/0102173 A1 May 5, 2011

(51) Int. Cl.
*G08B 1/08* (2006.01)
*G08B 23/00* (2006.01)
*A61B 5/00* (2006.01)

(52) U.S. Cl. ........... 340/539.13; 340/539.12; 340/573.1; 340/573.4; 340/286.14; 600/301; 128/903; 701/400

(58) Field of Classification Search ............. 340/539.13, 340/539.12, 573.4, 286.14
See application file for complete search history.

(56) References Cited

U.S. PATENT DOCUMENTS 4,918,432 A 4/1990 Pauley et al.
5,917,414 A 6/1999 Oppelt et al.
6,006,021 A 12/1999 Tognazzini
6,181,253 B1 1/2001 Eschenbach et al.
6,243,039 B1 6/2001 Elliot
6,489,893 B1 12/2002 Richards et al.
6,492,906 B1 12/2002 Richards et al.
6,611,783 B2 8/2003 Kelly, Jr. et al.
6,674,368 B2 1/2004 Hawkins et al.
6,983,202 B2 1/2006 Sanqunetti
7,038,589 B2 5/2006 Schmidt et al.
7,138,914 B2 11/2006 Culpepper et al.
7,164,986 B2 1/2007 Humphries et al.
7,340,260 B2 3/2008 McAlexander
7,353,034 B2 4/2008 Haney
2004/0172403 A1 9/2004 Steele et al.
2004/0225203 A1 11/2004 Jemison et al.
2005/0086261 A1 4/2005 Mammone
2005/0113721 A1 * 5/2005 Reed et al. .................... 600/595
2006/0229503 A1 10/2006 Fluegel
2006/0287872 A1 12/2006 Simrell
2007/0171046 A1 * 7/2007 Diem ........................ 340/539.13
2008/0094230 A1 4/2008 Mock et al.
2008/0305806 A1 12/2008 Jung et al.
2009/0227877 A1 9/2009 Tran

OTHER PUBLICATIONS

International Search Report for PCT Application No. PCT/US2010/054935 dated Jan. 3, 2011.

* cited by examiner

*Primary Examiner* — Donnie Crosland

(74) *Attorney, Agent, or Firm* — Ishimaru & Associates LLP; Mikio Ishimaru; Stanley Chang

(57) ABSTRACT

A method of operation of a navigation system includes: receiving a context boundary; receiving a boundary criteria for the context boundary; identifying a personal physical characteristic for monitoring a monitored person; detecting a personal noncompliance to the boundary criteria based on a discrepancy of the personal physical characteristic; and generating an alert based on the personal noncompliance for displaying on a device.

20 Claims, 7 Drawing Sheets

NAVIGATION SYSTEM WITH CONTEXT BOUNDARY MONITORING MECHANISM AND METHOD OF OPERATION THEREOF

CROSS-REFERENCE TO RELATED APPLICATION(S)

The present application contains subject matter related to a concurrently filed U.S. patent application by Aliasgar Mumtaz Husain, Hanhong Li, and Hongwei Feng entitled “NAVIGATION SYSTEM WITH MONITORING MECHANISM AND METHOD OF OPERATION THEREOF”. The related application is assigned to TeleNav, Inc. and is identified by docket number 59-038. The subject matter thereof is incorporated herein by reference thereto.

TECHNICAL FIELD

The present invention relates generally to a navigation system and more particularly to a navigation system with context boundary monitoring mechanism.

BACKGROUND ART

Modern portable consumer and industrial electronics, especially client devices such as navigation systems, cellular phones, portable digital assistants, and combination devices, are providing increasing levels of functionality to support modern life including location-based information services. Numerous technologies have been developed to utilize this new functionality.

As users become more empowered with the growth of mobile location based service devices, new and old paradigms begin to take advantage of this new device space. There are many technological solutions to take advantage of this new device location opportunity. One existing approach is to use location information to provide navigation services such as a global positioning system (GPS) for a car or on a mobile device such as a cell phone or a personal digital assistant (PDA).

Location based services allow users to create, transfer, store, and/or consume information that affects the “real world”. One such use of location-based services is to provide personal safety, security, and surveillance features.

Navigation systems and location based services enabled systems have been incorporated in automobiles, notebooks, handheld devices, and other portable products. Today, these systems aid users by incorporating available, real-time relevant information, such as maps, directions, local businesses, or other points of interest (POI). The real-time information provides invaluable relevant information, when available or in service areas.

In response to consumer demand, navigation systems are providing ever-increasing functionality. Current navigations systems lack features that include monitoring and tracking of people. The lack of these features entails security and safety risks. Guardians of incapacitated adults, senior citizens, children, legal minors, and people with mental disabilities lack tools and features to keep them safe.

Thus, a need still remains for a navigation system with context boundary monitoring mechanism providing low cost, improved functionality, and improved reliability. In view of the ever-increasing need to save costs and improve efficiencies, it is increasingly critical that answers be found to these problems. In view of the ever-increasing commercial competitive pressures, along with growing consumer expectations and the diminishing opportunities for meaningful product differentiation in the marketplace, it is critical that answers be found for these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

The present invention provides a method of operation of a navigation system including: receiving a context boundary; receiving a boundary criteria for the context boundary; identifying a personal physical characteristic for monitoring a monitored person; detecting a personal noncompliance to the boundary criteria based on a discrepancy of the personal physical characteristic; and generating an alert based on the personal noncompliance for displaying on a device.

The present invention provides a navigation system including: a context module for receiving a context boundary; a criteria module, coupled to the context module, for receiving a boundary criteria for the context boundary; an identify physical module, coupled to the criteria module, for identifying a personal physical characteristic for monitoring a monitored person; a monitor criteria module, coupled to the identify physical module, for detecting a personal noncompliance to the boundary criteria based on a discrepancy of the personal physical characteristic; and a generate alert module, coupled to the monitor criteria module, for generating an alert based on the personal noncompliance for displaying on a device.

Certain embodiments of the invention have other steps or elements in addition to or in place of those mentioned above. The steps or elements will become apparent to those skilled in the art from a reading of the following detailed description when taken with reference to the accompanying drawings.

BEST MODE FOR CARRYING OUT THE INVENTION

Figure 1:
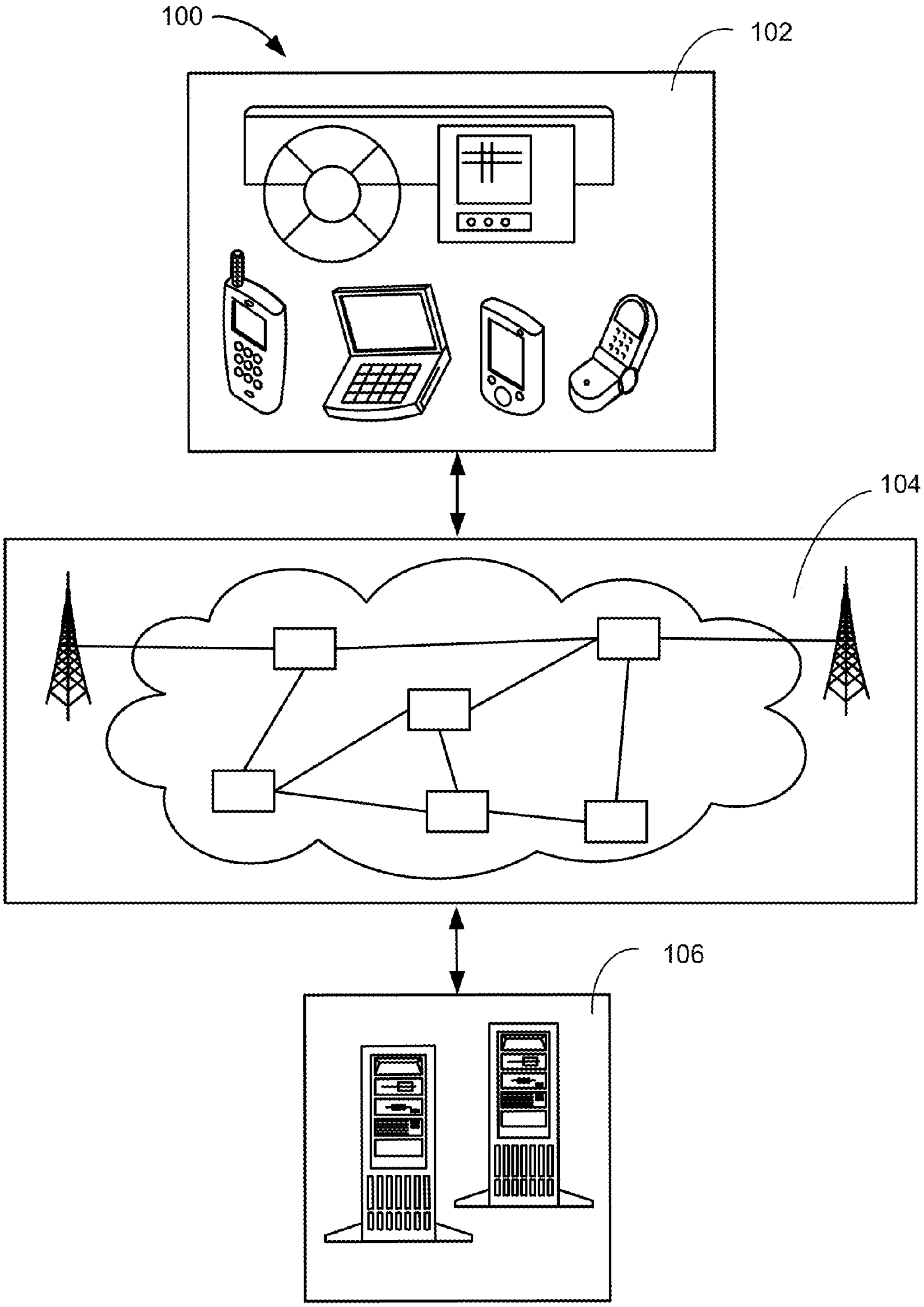
FIG. 1 is a navigation system with context boundary monitoring mechanism in a first embodiment of the present invention.

The following embodiments are described in sufficient detail to enable those skilled in the art to make and use the invention. It is to be understood that other embodiments would be evident based on the present disclosure, and that system, process, or mechanical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known circuits, system configurations, and process steps are not disclosed in detail.

The drawings showing embodiments of the system are semi-diagrammatic and not to scale and, particularly, some of the dimensions are for the clarity of presentation and are shown exaggerated in the drawing FIGs. Similarly, although the views in the drawings for ease of description generally show similar orientations, this depiction in the FIGs. is arbitrary for the most part. Generally, the invention can be operated in any orientation.

Where multiple embodiments are disclosed and described having some features in common, for clarity and ease of illustration, description, and comprehension thereof, similar and like features one to another will ordinarily be described with similar reference numerals. The embodiments have been numbered first embodiment, second embodiment, etc. as a matter of descriptive convenience and are not intended to have any other significance or provide limitations for the present invention.

One skilled in the art would appreciate that the format with which navigation information is expressed is not critical to some embodiments of the invention. For example, in some embodiments, navigation information is presented in the format of (X, Y), where X and Y are two ordinates that define the geographic location, i.e., a position of a user.

In an alternative embodiment, navigation information is presented by longitude and latitude related information. In a further embodiment of the present invention, the navigation information also includes a velocity element comprising a speed component and a heading component.

The term "relevant information" referred to herein comprises the navigation information described as well as information relating to points of interest to the user, such as local business, hours of businesses, types of businesses, advertised specials, traffic information, maps, local events, and nearby community or personal information.

The term "module" referred to herein, can include software, hardware, or a combination thereof. For example, the software can be machine code, firmware, embedded code, and application software. Also for example, the hardware can be circuitry, processor, computer, integrated circuit, integrated circuit cores, a pressure sensor, an inertial sensor, a microelectromechanical system (MEMS), passive devices, or a combination thereof.

The term "criteria" referred to herein, can include rules or conditions that can affect the actions of the navigation system. The criteria can be user-defined rules, standards, or conditions. For example, when a criterion is met, exceeded, broken, or violated, the navigation system can generate an alert for display on a screen. The criteria can be user-defined or assigned by the navigation system.

Referring now to FIG. 1, therein is shown a navigation system 100 with context boundary monitoring mechanism in a first embodiment of the present invention. The navigation system 100 includes a first device 102, such as a client or a server, connected to a second device 106, such as a client or server, with a communication path 104, such as a wireless or wired network.

For example, the first device 102 can be of any of a variety of mobile devices, such as a cellular phone, personal digital assistant, a notebook computer, automotive telemetric navigation system, or other multi-functional mobile communication or entertainment device. The first device 102 can be a standalone device, or can be incorporated with a vehicle, for example a car, truck, bus, or train. The first device 102 can couple to the communication path 104 to communicate with the second device 106.

For illustrative purposes, the navigation system 100 is described with the first device 102 as a mobile computing device, although it is understood that the first device 102 can be different types of computing devices. For example, the first device 102 can also be a non-mobile computing device, such as a server, a server farm, or a desktop computer.

The second device 106 can be any of a variety of centralized or decentralized computing devices. For example, the second device 106 can be a computer, grid-computing resources, a virtualized computer resource, cloud computing resource, routers, switches, peer-to-peer distributed computing devices, or a combination thereof.

The second device 106 can be centralized in a single computer room, distributed across different rooms, distributed across different geographical locations, embedded within a telecommunications network. The second device 106 can have a means for coupling with the communication path 104 to communicate with the first device 102. The second device 106 can also be a client type device as described for the first device 102.

In another example, the first device 102 can be a particularized machine, such as a mainframe, a server, a cluster server, rack mounted server, or a blade server, or as more specific examples, an IBM System z10™ Business Class mainframe or a HP ProLiant ML™ server. Yet another example, the second device 106 can be a particularized machine, such as a portable computing device, a thin client, a notebook, a netbook, a smartphone, personal digital assistant, or a cellular phone, and as specific examples, an Apple iPhone™, Palm Centro™, or Moto Q Global™.

For illustrative purposes, the navigation system 100 is described with the second device 106 as a non-mobile computing device, although it is understood that the second device 106 can be different types of computing devices. For example, the second device 106 can also be a mobile computing device, such as notebook computer, another client device, or a different type of client device. The second device 106 can be a standalone device, or can be incorporated with a vehicle, for example a car, truck, bus, or train.

Also for illustrative purposes, the navigation system 100 is shown with the second device 106 and the first device 102 as end points of the communication path 104, although it is understood that the navigation system 100 can have a different partition between the first device 102, the second device 106, and the communication path 104. For example, the first device 102, the second device 106, or a combination thereof can also function as part of the communication path 104.

The communication path 104 can be a variety of networks. For example, the communication path 104 can include wireless communication, wired communication, optical, ultrasonic, or the combination thereof. Satellite communication, cellular communication, Bluetooth, Infrared Data Association standard (IrDA), wireless fidelity (WiFi), and worldwide interoperability for microwave access (WiMAX) are examples of wireless communication that can be included in the communication path 104. Ethernet, digital subscriber line (DSL), fiber to the home (FTTH), and plain old telephone service (POTS) are examples of wired communication that can be included in the communication path 104.

Further, the communication path 104 can traverse a number of network topologies and distances. For example, the communication path 104 can include direct connection, personal area network (PAN), local area network (LAN), metropolitan area network (MAN), wide area network (WAN) or any combination thereof.

Figure 2:
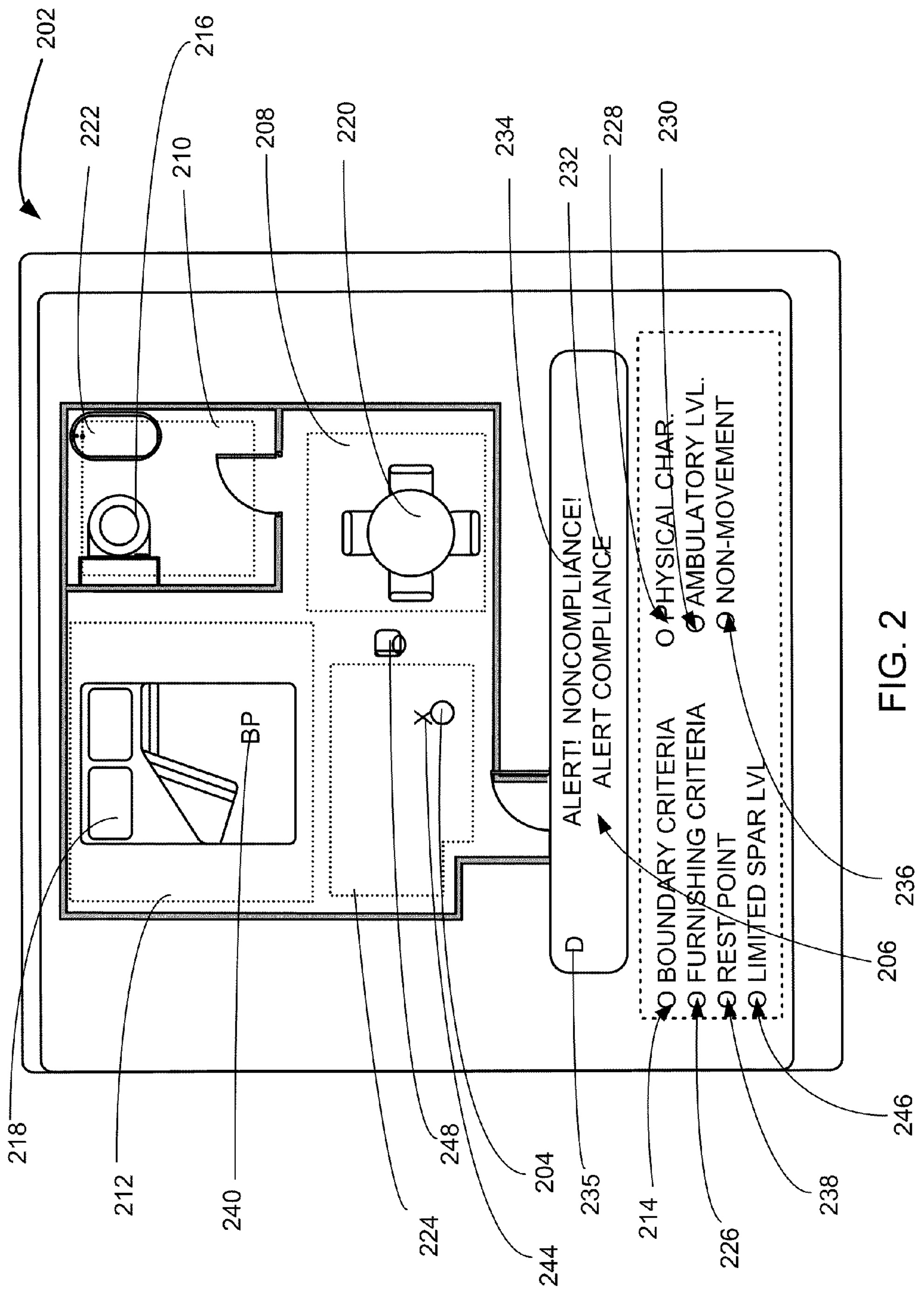
FIG. 2 is a first example of a display interface of the first device.

Referring now to FIG. 2, therein is shown a first example of a display interface 202 of the first device 102. The display interface 202 can depict a monitored person 204, an alert 206, a context boundary 208, a restroom boundary 210, a bedroom boundary 212, and a boundary criteria 214. The display interface 202 can also depict a context furnishing 216, a bed 218, a dining set 220, a bathtub 222, an open space boundary 224, a furnishing criteria 226.

The display interface 202 can further depict a personal physical characteristic 228, a limited ambulatory level 230, and a personal compliance 232, a personal noncompliance 234, a discrepancy 235, a non-movement time limit 236. The display interface 202 can yet further depict a rest point 238, a personal bedsore position 240, a personal location 244, a limited separation level 246, and a wheelchair 248.

The display interface 202 can depict a one-bedroom studio apartment and can graphically display the bed 218, the bathtub 222, and the dining set 220. The monitored person 204 can represent an incapacitated adult, senior citizen, person with mental disabilities, legal ward, guest, visitor, prisoner, criminal, and parolee to be monitored on the display interface 202.

The monitored person 204 can have a guardian that is legally responsible for the monitored person 204. Legal wards are people under the supervision or protection of a legal guardian. The monitored person 204 can be displayed as a dot or icon on the display interface 202. The monitored person 204 can be holding or wearing a device that emits a tracking signal such as a global positioning system (GPS) signal or a cellular signal for triangulation. For example, this device can be the first device 102 or a tracking bracelet.

For clarity in explaining the present invention, the examples provided below can refer to the monitored person 204 as human beings but this example does not imply limitations. The present invention can also apply to animals and live stock such as dogs, cats, and cattle. Again, the present invention's use of the term, the monitored person 204 is only for clarity in explanation.

The alert 206 can represent a warning or notification based on the actions of the monitored person 204. The alert 206 can be implemented in a number of ways. For example, the alert 206 can be a pop up message on the display interface 202. The alert 206 can also be an audio alarm. The alert 206 can occur based on user-defined criteria, rules, or conditions. The alert 206 can display information regarding the monitored person 204. For example, the alert 206 can display the time, place, action, and other pertinent information on the display interface 202.

The context boundary 208 can represent a specific geographic region within which the monitored person 204 will be monitored. The context boundary 208 can cover a room in a house, a portion of a room, an entire building and outdoor region. The context boundary 208 can be customized to have characteristics, properties, conditions, or a context associated to the context boundary 208 for generating the alert 206. The context boundary 208 can be set up to cover many areas or rooms of a house, such as kitchens, restrooms, and bedrooms. The different types of rooms can have different criteria or properties that can generate the alert 206.

For example, restrooms can be assigned to the restroom boundary 210 as the context boundary 208 for a restroom. Bedrooms can be assigned to the bedroom boundary 212 as the context boundary 208 for the bedroom. The restroom boundary 210 can have different rules or criteria that can generate the alert 206 than the bedroom boundary 212. The context boundary 208 can also be configured to cover a user-defined shape to cover the contours of a room in a house or building.

The boundary criteria 214 can represent the rules, context, properties, or criteria associated with the context boundary 208 that can be used to trigger the generating of the alert 206. The boundary criteria 214 can be associated with the context boundary 208, the restroom boundary 210, and the bedroom boundary 212.

On the display interface 202, the boundary criteria 214 can be depicted as informational text displaying the criteria. The boundary criteria 214 can represent the selected criteria that can generate the alert 206, such as restrictions for being inside the context boundary 208. For example, the boundary criteria 214 can be a complete restriction or time limit inside the context boundary 208. Other examples of the boundary criteria 214 will be explained below.

The context furnishing 216 can represent an object, such as furniture, fixtures, fitments, equipment, and appliances for monitoring a person's interactions. For example, the context furnishing 216 can include beds, sofas, chairs, toilets, sinks, benches, and appliances. The display interface 202 can depict a toilet as the context furnishing 216. The bed 218, the dining set 220, the wheelchair 248, and the bathtub 222 can represent other examples of the context furnishing 216. The open space boundary 224 can represent the context boundary 208 with none of the context furnishing 216 or other objects in the context boundary 208.

The furnishing criteria 226 can represent rules, context, properties, or criteria associated with the context furnishing 216 that can be used to trigger the generating of the alert 206. On the display interface 202, the furnishing criteria 226 can be depicted as informational text displaying the furnishing criteria 226. The furnishing criteria 226 can include restrictions and time limits of the proximity of the monitored person 204 and the context furnishing 216.

The personal physical characteristic 228 can represent abilities or attributes of the monitored person 204. For example, the personal physical characteristic 228 can represent the monitored person's personal attributes for particular physical tasks, such as the person's walking speed, duration in the ability to remain standing, and resting positions. Changes or deviations from the personal physical characteristic 228 can suggest problems like sudden falls or injuries that can trigger the alert 206. For example, the personal physical characteristic 228 can represent how quickly the monitored person 204 can climb up stairs or how long the monitored person 204 usually sleeps or rests on the context furnishing 216 such as the bed 218.

The personal physical characteristic 228 can also correspond or be linked to the boundary criteria 214, the furnishing criteria 226, or the combination thereof to generate the alert 206. The personal physical characteristic 228 can represent different abilities or attributes for different types of the context boundary 208 and the context furnishing 216.

For example, the monitored person 204 can be a senior citizen with the personal physical characteristic 228 of very slow walking speed for a room with many obstacles. In the open space boundary 224, such as an empty room, the personal physical characteristic 228 can be different, such as faster walking speed. The personal physical characteristic 228 can be user defined or automatically identified by the navigation system 100 of FIG. 1.

The limited ambulatory level 230 can represent limited walking ability of the monitored person 204 for the personal physical characteristic 228. The limited ambulatory level 230 can be user-defined or automatically identified by the navigation system 100. For example, the navigation system 100 can determine if the monitored person 204 has trouble walking by measuring the speed, identifying staggering in the walking course, and the frequency of rest stops of the monitored person 204. The limited ambulatory level 230 can be displayed on the display interface 202 as informational text.

The personal physical characteristic 228 can be obtained through other means. For example, medical records for the monitored person 204 can provide the personal physical characteristic 228. A person with severe congestive heart failure will likely have the personal physical characteristic 228 as the limited ambulatory level 230.

The personal compliance 232 can represent when the monitored person 204 conforms to the boundary criteria 214, the furnishing criteria 226, or the combination thereof. Depending on the boundary criteria 214 and the furnishing criteria 226, the personal compliance 232 can trigger or cancel the generating of the alert 206.

The personal noncompliance 234 can represent when the monitored person 204 does not conform or the personal physical characteristic 228 is incompatible to the boundary criteria 214, the furnishing criteria 226, or a combination thereof. Depending on the boundary criteria 214 and the furnishing criteria 226, the personal noncompliance 234 can trigger or cancel the generating of the alert 206.

The discrepancy 235 can represent when the monitored person 204 is behaving, moving, or performing an action in such a way that does not conform to past records of the personal physical characteristic 228. For example, the navigation system 100 can detect the discrepancy 235 if the monitored person 204 begins to walk differently than the past record of the limited ambulatory level 230. If the limited ambulatory level 230 reflected a slow staggered walk and the monitored person 204 begins to run, the discrepancy 235 can be detected. For example, the discrepancy 235 can be displayed on the display interface 202 as an icon of the letter "D."

The non-movement time limit 236 can represent criteria for generating the alert 206. If the monitored person 204 remains stationary beyond the non-movement time limit 236, the alert 206 can be generated. The non-movement time limit 236 can represent the boundary criteria 214, the furnishing criteria 226, or a combination thereof.

For example, the non-movement time limit 236 can apply to a piece of furniture as well as a room assigned as the context boundary 208. The non-movement time limit 236 can be set to thirty minutes for the restroom boundary 210 or the context furnishing 216, such as the bathtub 222 for generating the alert 206.

The rest point 238 can represent an example of the furnishing criteria 226 for the context furnishing 216. The rest point 238 can represent when the context furnishing 216, such as a chair, table, or sofa, is an object where the monitored person 204 can stop to rest. The non-movement time limit 236 can temporally be disabled or adjusted when the monitored person 204 is resting at the context furnishing 216 that is the rest point 238.

For example, the non-movement time limit 236 can be set to thirty minutes. If the monitored person 204 is at the rest point 238, such as a sofa, the non-movement time limit 236 can be adjusted to two hours as long as the monitored person 204 remains at the rest point 238.

The personal bedsore position 240 can represent the personal physical characteristic 228 in which the monitored person 204 is laying down in a position that would cause bedsores. The personal bedsore position 240 can be automatically determined by the navigation system 100 or user-defined. The personal bedsore position 240 will be described in more detailed later.

When the monitored person 204 enters the personal bedsore position 240, the display interface 202 can display this situation as an icon with the letters "BP." If the monitored person 204 shifts position or stands up, the icon displaying the personal bedsore position 240 can disappear from the display interface 202.

The personal location 244 can represent the location of the monitored person 204. The limited separation level 246 can represent the furnishing criteria 226 that generates the alert 206 when the monitored person 204 is separated from the context furnishing 216, such as the wheelchair 248 or the bed 218. For example, the alert 206 can be generated if the monitored person 204 falls out of the wheelchair 248 or the bed 218.

Figure 3:
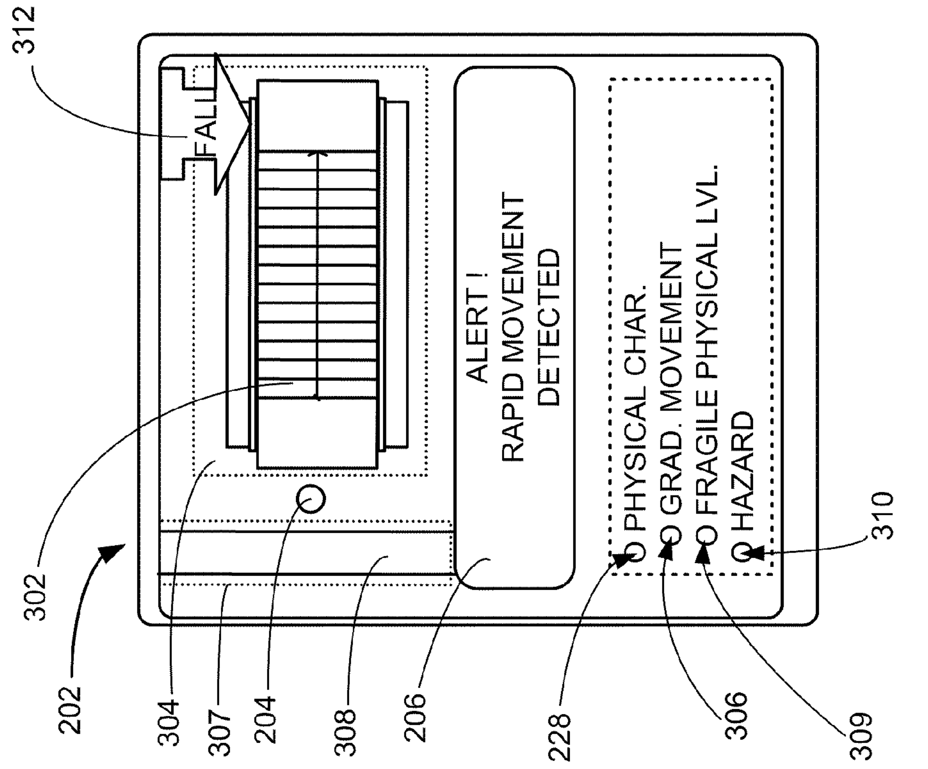
FIG. 3 is a second example of a display interface of the first device.

Referring now to FIG. 3, therein is shown a second example of the display interface 202 of the first device 102. The display interface 202 can depict the monitored person 204, the alert 206, and the personal physical characteristic 228. The display interface 202 can also depict a stairway 302, a stairway boundary 304, a gradual movement level 306, a crowded path boundary 307, a crowded path 308, a fragile physical level 309, a hazard 310, and a personal rapid movement 312.

The display interface 202 can depict a situation where the monitored person 204 is about to descend the stairway 302. For illustrative purposes, the monitored person 204 has just left the crowded path 308. The crowded path 308 can represent a road in a park with many pedestrians and bikers. The crowded path boundary 307 can represent the context boundary 208 of FIG. 2 for the crowded path 308. The stairway boundary 304 can represent the context boundary 208 for the stairway 302.

The gradual movement level 306 can be the personal physical characteristic 228 that can represent the typical or usual moving speed and moving behavior of the monitored person 204. For example, if the monitored person 204 uses the wheelchair 248 of FIG. 2, the gradual movement level 306 can reflect the usual speed of the monitored person 204 moving in the wheelchair 248. The gradual movement level 306 can be user-defined or automatically identified by the navigation system 100. The gradual movement level 306 can also represent a walking cadence of the monitored person 204. The gradual movement level 306 can be displayed on the display interface 202 as informational text.

The fragile physical level 309 can be the personal physical characteristic 228 for the monitored person 204 who can be fragile and highly susceptible to injury for generating the alert 206. For example, the fragile physical level 309 can be assigned to the monitored person 204 and the alert 206 can be generated when the monitored person 204 enters into a restricted area that is incompatible with the fragile physical level 309. The fragile physical level 309 can be user-defined. The fragile physical level 309 can be displayed on the display interface 202 as informational text.

The hazard 310 can represent the boundary criteria 214 of FIG. 2 for the context boundary 208 that is incompatible with the fragile physical level 309. For example, the hazard 310 can represent the boundary criteria 214 that prohibits or cautions the monitored person 204 from the context boundary 208 because of potential dangers in the context boundary 208.

For example, the dangers or hazards can include crowded and congressed areas where little children or adults are running or playing. In the display interface 202, the crowded path boundary 307 can have the boundary criteria 214 that is designated as the hazard 310.

In a nursing home example, the context boundary 208 can cover the lobby where grandchildren might play. The lobby area can have the hazard 310 as the boundary criteria 214 for the context boundary 208. This area can have many children playing which might be dangerous for senior citizens in the area. The alert 206 can be generated if the monitored person 204 with the fragile physical level 309 enters the context boundary 208.

The personal rapid movement 312 can represent a sudden and quick movement that is not consistent with the gradual movement level 306. The personal rapid movement 312 can represent the discrepancy 235 of FIG. 2 to the gradual movement level 306. The personal rapid movement 312 can suggest a sudden fall or tripping of the monitored person 204.

The personal rapid movement 312 can be detected by a sudden elevation change and sudden change of motion of the monitored person 204 that is consistent with a fall. The personal rapid movement 312 can be displayed on the display interface 202 as icon reflecting a fall.

Figure 4:
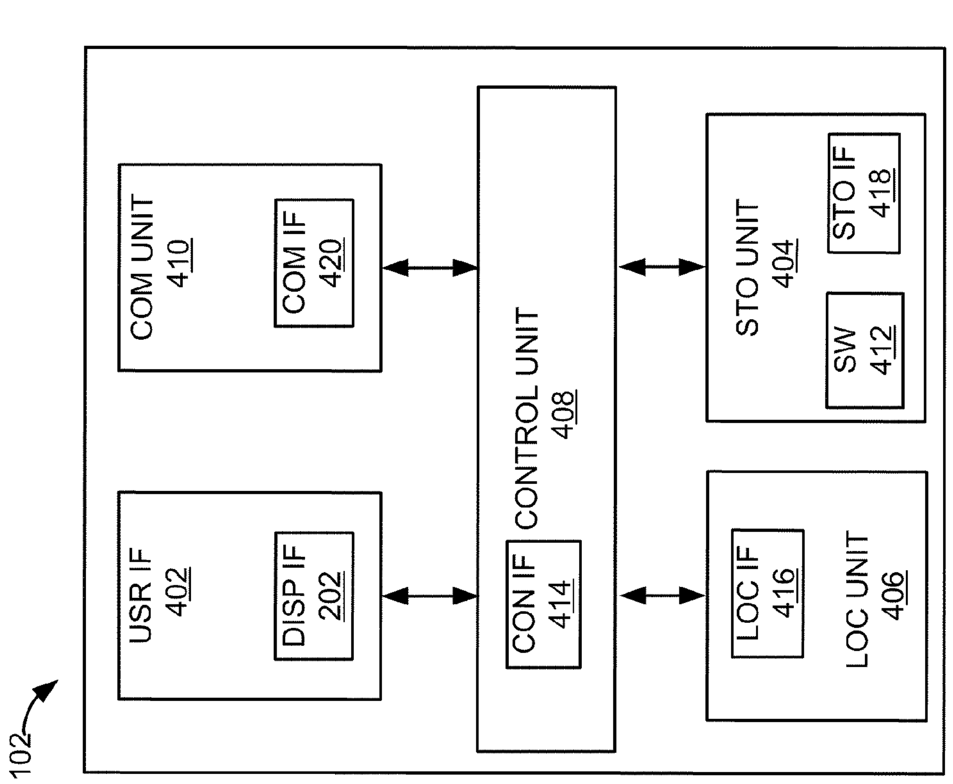
FIG. 4 is an exemplary block diagram of the first device.

Referring now to FIG. 4, therein is shown an exemplary block diagram of the first device 102. The first device 102 can include a user interface 402, a storage unit 404, a location unit 406, a control unit 408, and a communication unit 410.

The user interface 402 allows a user (not shown) to interface and interact with the first device 102. The user interface 402 can include an input device and an output device. Examples of the input device of the user interface 402 can include a keypad, a touchpad, soft-keys, a keyboard, a microphone, or any combination thereof to provide data and communication inputs. Examples of the output device of the user interface 402 can include the display interface 202. The display interface 202 can include a display, a projector, a video screen, a speaker, or any combination thereof.

The control unit 408 can execute a software 412 to provide the intelligence of the navigation system 100 of FIG. 1. The control unit 408 can operate the user interface 402 to display information generated by the navigation system 100. The control unit 408 can also execute the software 412 for the other functions of the navigation system 100, including receiving location information from the location unit 406. The control unit 408 can further execute the software 412 for interaction with the communication path 104 of FIG. 1 via the communication unit 410.

The control unit 408 can be implemented in a number of different manners. For example, the control unit 408 can be a processor, an embedded processor, a microprocessor, a hardware control logic, a hardware finite state machine (FSM), a digital signal processor (DSP), or a combination thereof.

The control unit 408 can include a controller interface 414. The controller interface 414 can be used for communication between the control unit 408 and other functional units in the first device 102. The controller interface 414 can also be used for communication that is external to the first device 102.

The controller interface 414 can receive information from the other functional units or from external sources, or can transmit information to the other functional units or to external destinations. The external sources and the external destinations refer to sources and destinations external to the first device 102.

The controller interface 414 can be implemented in different ways and can include different implementations depending on which functional units or external units are being interfaced with the controller interface 414. For example, the controller interface 414 can be implemented with a pressure sensor, an inertial sensor, a microelectromechanical system (MEMS), optical circuitry, waveguides, wireless circuitry, wireline circuitry, or a combination thereof.

The location unit 406 can generate location information, current heading, and current speed of the first device 102, as examples. The location unit 406 can be implemented in many ways. For example, the location unit 406 can function as at least a part of a global positioning system (GPS), an inertial navigation system, a cellular-tower location system, a pressure location system, or any combination thereof.

The location unit 406 can include a location interface 416. The location interface 416 can be used for communication between the location unit 406 and other functional units in the first device 102. The location interface 416 can also be used for communication that is external to the first device 102.

The location interface 416 can receive information from the other functional units or from external sources, or can transmit information to the other functional units or to external destinations. The external sources and the external destinations refer to sources and destinations external to the first device 102.

The location interface 416 can include different implementations depending on which functional units or external units are being interfaced with the location unit 406. The location interface 416 can be implemented with technologies and techniques similar to the implementation of the controller interface 414.

The storage unit 404 can store the software 412. The storage unit 404 can also store the relevant information, such as advertisements, points of interest (POI), navigation routing entries, or any combination thereof.

The storage unit 404 can be a volatile memory, a nonvolatile memory, an internal memory, an external memory, or a combination thereof. For example, the storage unit 404 can be a nonvolatile storage such as non-volatile random access memory (NVRAM), Flash memory, disk storage, or a volatile storage such as static random access memory (SRAM).

The storage unit 404 can include a storage interface 418. The storage interface 418 can be used for communication between the location unit 406 and other functional units in the first device 102. The storage interface 418 can also be used for communication that is external to the first device 102.

The storage interface 418 can receive information from the other functional units or from external sources, or can transmit information to the other functional units or to external destinations. The external sources and the external destinations refer to sources and destinations external to the first device 102.

The storage interface 418 can include different implementations depending on which functional units or external units are being interfaced with the storage unit 404. The storage interface 418 can be implemented with technologies and techniques similar to the implementation of the controller interface 414.

The communication unit 410 can enable external communication to and from the first device 102. For example, the communication unit 410 can permit the first device 102 to communicate with the second device 106 of FIG. 1, an attachment, such as a peripheral device or a computer desktop, and the communication path 104.

The communication unit 410 can also function as a communication hub allowing the first device 102 to function as part of the communication path 104 and not limited to be an end point or terminal unit to the communication path 104. The communication unit 410 can include active and passive components, such as microelectronics or an antenna, for interaction with the communication path 104.

The communication unit 410 can include a communication interface 420. The communication interface 420 can be used for communication between the communication unit 410 and other functional units in the first device 102. The communication interface 420 can receive information from the other functional units or can transmit information to the other functional units.

The communication interface 420 can include different implementations depending on which functional units are being interfaced with the communication unit 410. The communication interface 420 can be implemented with technologies and techniques similar to the implementation of the controller interface 414.

For illustrative purposes, the navigation system 100 is shown with the partition having the user interface 402, the storage unit 404, the location unit 406, the control unit 408, and the communication unit 410 although it is understood that the navigation system 100 can have a different partition. For example, the software 412 can be partitioned differently such that some or all of its function can be in the control unit 408, the location unit 406, and the communication unit 410. In addition, the first device 102 can include other functional units not shown in FIG. 4 for clarity.

The functional units in the first device 102 can work individually and independently of the other functional units. The first device 102 can work individually and independently from the second device 106 and the communication path 104.

Figure 5:
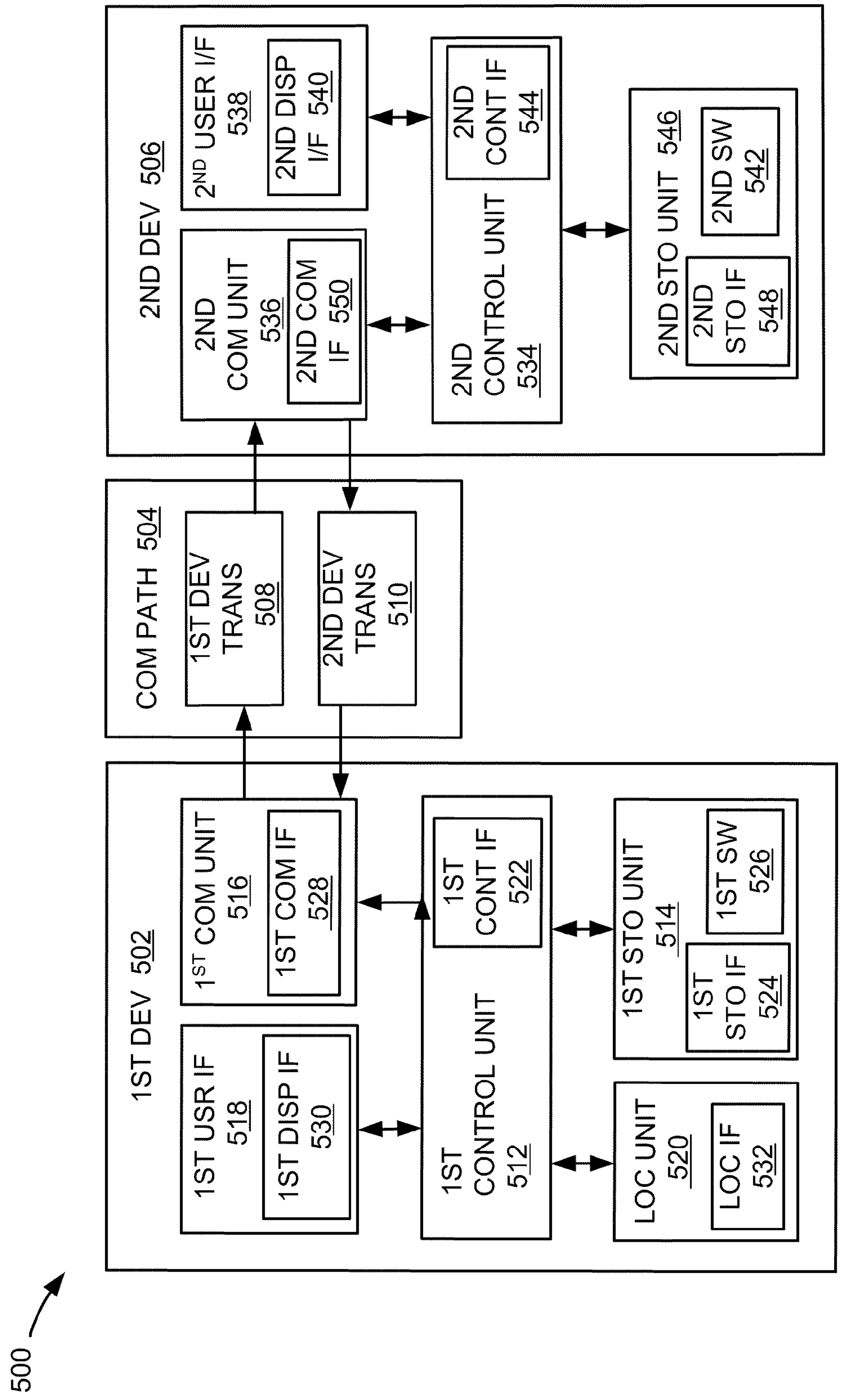
FIG. 5 is an exemplary block diagram of a navigation system with context boundary monitoring mechanism in a second embodiment of the present invention.

Referring now to FIG. 5, therein is shown an exemplary block diagram of a navigation system 500 with context boundary monitoring mechanism in a second embodiment of the present invention. The navigation system 500 can include a first device 502, a communication path 504, and a second device 506.

The first device 502 can communicate with the second device 506 over the communication path 504. For example, the first device 502, the communication path 504, and the second device 506 can be the first device 102 of FIG. 1, the communication path 104 of FIG. 1, and the second device 106 of FIG. 1, respectively. The screen shot shown on the display interface 202 described in FIG. 2 can represent the screen shot for the navigation system 500.

The first device 502 can send information in a first device transmission 508 over the communication path 504 to the second device 506. The second device 506 can send information in a second device transmission 510 over the communication path 504 to the first device 502.

For illustrative purposes, the navigation system 500 is shown with the first device 502 as a client device, although it is understood that the navigation system 500 can have the first device 502 as a different type of device. For example, the first device 502 can be a server.

Also for illustrative purposes, the navigation system 500 is shown with the second device 506 as a server, although it is understood that the navigation system 500 can have the second device 506 as a different type of device. For example, the second device 506 can be a client device.

For brevity of description in this embodiment of the present invention, the first device 502 will be described as a client device and the second device 506 will be described as a server device. The present invention is not limited to this selection for the type of devices. The selection is an example of the present invention.

The first device 502 can include a first control unit 512, a first storage unit 514, a first communication unit 516, a first user interface 518, and a location unit 520. The first device 502 can be similarly described by the first device 102.

The first control unit 512 can include a first control interface 522. The first control unit 512 and the first control interface 522 can be similarly described as the control unit 408 of FIG. 4 and the controller interface 414 of FIG. 4, respectively.

The first storage unit 514 can include a first storage interface 524. The first storage unit 514 and the first storage interface 524 can be similarly described as the storage unit 404 of FIG. 4 and the storage interface 418 of FIG. 4, respectively. A first software 526 can be stored in the first storage unit 514.

The first communication unit 516 can include a first communication interface 528. The first communication unit 516 and the first communication interface 528 can be similarly described as the communication unit 410 of FIG. 4 and the communication interface 420 of FIG. 4, respectively.

The first user interface 518 can include a first display interface 530. The first user interface 518 and the first display interface 530 can be similarly described as the user interface 402 of FIG. 4 and the display interface 202 of FIG. 4, respectively.

The location unit 520 can include a location interface 532. The location unit 520 and the location interface 532 can be similarly described as the location unit 406 of FIG. 4 and the location interface 416 of FIG. 4, respectively.

The performance, architectures, and type of technologies can also differ between the first device 102 and the first device 502. For example, the first device 102 can function as a single device embodiment of the present invention and can have a higher performance than the first device 502. The first device 502 can be similarly optimized for a multiple device embodiment of the present invention.

For example, the first device 102 can have a higher performance with increased processing power in the control unit 408 compared to the first control unit 512. The storage unit 404 can provide higher storage capacity and access time compared to the first storage unit 514.

Also for example, the first device 502 can be optimized to provide increased communication performance in the first communication unit 516 compared to the communication unit 410. The first storage unit 514 can be sized smaller compared to the storage unit 404. The first software 526 can be smaller than the software 412 of FIG. 4.

The second device 506 can be optimized for implementing the present invention in a multiple device embodiment with the first device 502. The second device 506 can provide the additional or higher performance processing power compared to the first device 502. The second device 506 can include a second control unit 534, a second communication unit 536, and a second user interface 538.

The second user interface 538 allows a user (not shown) to interface and interact with the second device 506. The second user interface 538 can include an input device and an output device. Examples of the input device of the second user interface 538 can include a keypad, a touchpad, soft-keys, a keyboard, a microphone, or any combination thereof to provide data and communication inputs. Examples of the output device of the second user interface 538 can include a second display interface 540. The second display interface 540 can include a display, a projector, a video screen, a speaker, or any combination thereof.

The second control unit 534 can execute a second software 542 to provide the intelligence of the second device 106 of the navigation system 500. The second software 542 can operate in conjunction with the first software 526. The second control unit 534 can provide additional performance compared to the first control unit 512 or the control unit 408.

The second control unit 534 can operate the second user interface 538 to display information. The second control unit 534 can also execute the second software 542 for the other functions of the navigation system 500, including operating the second communication unit 536 to communicate with the first device 502 over the communication path 504.

The second control unit 534 can be implemented in a number of different manners. For example, the second control unit 534 can be a processor, an embedded processor, a microprocessor, a hardware control logic, a hardware finite state machine (FSM), a digital signal processor (DSP), or a combination thereof.

The second control unit 534 can include a second controller interface 544. The second controller interface 544 can be used for communication between the second control unit 534 and other functional units in the second device 506. The second controller interface 544 can also be used for communication that is external to the second device 506.

The second controller interface 544 can receive information from the other functional units or from external sources, or can transmit information to the other functional units or to external destinations. The external sources and the external destinations refer to sources and destinations external to the second device 506.

The second controller interface 544 can be implemented in different ways and can include different implementations depending on which functional units or external units are being interfaced with the second controller interface 544. For example, the second controller interface 544 can be implemented with a pressure sensor, an inertial sensor, a microelectromechanical system (MEMS), optical circuitry, waveguides, wireless circuitry, wireline circuitry, or a combination thereof.

A second storage unit 546 can store the second software 542. The second storage unit 546 can also store the relevant information, such as advertisements, points of interest (POI), navigation routing entries, or any combination thereof. The second storage unit 546 can be sized to provide the additional storage capacity to supplement the first storage unit 514.

For illustrative purposes, the second storage unit 546 is shown as a single element, although it is understood that the second storage unit 546 can be a distribution of storage elements. Also for illustrative purposes, the navigation system 500 is shown with the second storage unit 546 as a single hierarchy storage system, although it is understood that the navigation system 500 can have the second storage unit 546 in a different configuration. For example, the second storage unit 546 can be formed with different storage technologies forming a memory hierarchal system including different levels of caching, main memory, rotating media, or off-line storage.

The second storage unit 546 can be a volatile memory, a nonvolatile memory, an internal memory, an external memory, or a combination thereof. For example, the second storage unit 546 can be a nonvolatile storage such as nonvolatile random access memory (NVRAM), Flash memory, disk storage, or a volatile storage such as static random access memory (SRAM).

The second storage unit 546 can include a second storage interface 548. The second storage interface 548 can be used for communication between the location unit 406 and other functional units in the second device 506. The second storage interface 548 can also be used for communication that is external to the second device 506.

The second storage interface 548 can receive information from the other functional units or from external sources, or can transmit information to the other functional units or to external destinations. The external sources and the external destinations refer to sources and destinations external to the second device 506.

The second storage interface 548 can include different implementations depending on which functional units or external units are being interfaced with the second storage unit 546. The second storage interface 548 can be implemented with technologies and techniques similar to the implementation of the second controller interface 544.

The second communication unit 536 can enable external communication to and from the second device 506. For example, the second communication unit 536 can permit the second device 506 to communicate with the first device 502 over the communication path 504.

The second communication unit 536 can also function as a communication hub allowing the second device 506 to function as part of the communication path 504 and not limited to be an end point or terminal unit to the communication path 504. The second communication unit 536 can include active and passive components, such as microelectronics or an antenna, for interaction with the communication path 504.

The second communication unit 536 can include a second communication interface 550. The second communication interface 550 can be used for communication between the second communication unit 536 and other functional units in the second device 506. The second communication interface 550 can receive information from the other functional units or can transmit information to the other functional units.

The second communication interface 550 can include different implementations depending on which functional units are being interfaced with the second communication unit 536. The second communication interface 550 can be implemented with technologies and techniques similar to the implementation of the second controller interface 544.

The first communication unit 516 can couple with the communication path 504 to send information to the second device 506 in the first device transmission 508. The second device 506 can receive information in the second communication unit 536 from the first device transmission 508 of the communication path 504.

The second communication unit 536 can couple with the communication path 504 to send information to the first device 502 in the second device transmission 510. The first device 502 can receive information in the first communication unit 516 from the second device transmission 510 of the communication path 504. The navigation system 500 can be executed by the first control unit 512, the second control unit 534, or a combination thereof.

For illustrative purposes, the second device 106 is shown with the partition having the second user interface 538, the second storage unit 546, the second control unit 534, and the second communication unit 536, although it is understood that the second device 106 can have a different partition. For example, the second software 542 can be partitioned differently such that some or all of its function can be in the second control unit 534 and the second communication unit 536. In addition, the second device 506 can include other functional units not shown in FIG. 5 for clarity.

The functional units in the first device 502 can work individually and independently of the other functional units. The first device 502 can work individually and independently from the second device 506 and the communication path 504.

The functional units in the second device 506 can work individually and independently of the other functional units. The second device 506 can work individually and independently from the first device 502 and the communication path 504.

For illustrative purposes, the navigation system 500 is described by operation of the first device 502 and the second device 506. It is understood that the first device 502 and the second device 506 can operate any of the modules and functions of the navigation system 500. For example, the first device 502 is described to operate the location unit 520, although it is understood that the second device 506 can also operate the location unit 520.

Figure 6:
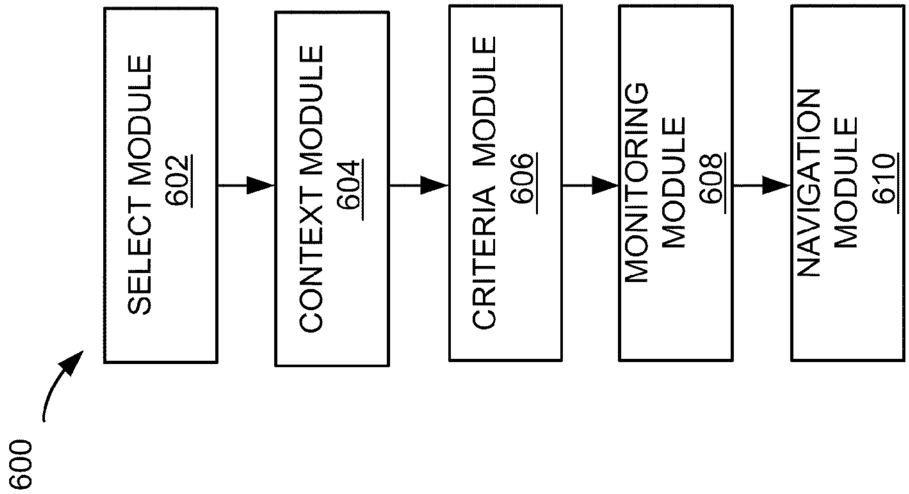
FIG. 6 is a navigation system with context boundary monitoring mechanism in a third embodiment of the present invention.

Referring now to FIG. 6, therein is shown a navigation system 600 with context boundary monitoring mechanism in a third embodiment of the present invention. The navigation system 600 can include a select module 602, a context module 604, a criteria module 606, a monitoring module 608, and a navigation module 610. In the navigation system 600, as an example, each module is indicated by a number and successively higher module numbers follow one another. Control flow can pass from one module to the next higher numbered module unless explicitly otherwise indicated.

The select module 602 can receive the selection for the monitored person 204 of FIG. 2. The selection can be user-initiated or automatically selected by the navigation system 600 and sent to the select module 602. For example, the select module 602 can prompt the user for tracking signal information for the monitored person 204 and then the select module 602 can receive the information requested. The navigation system 600 can also automatically detect tracking signals within the context boundary 208 of FIG. 2.

Different tracking signals can be received by the select module 602 for each of the monitored person 204 that are inputted into or detected by the navigation system 600. The select module 602 can receive user selections from the user interface 402 of FIG. 4.

The select module 602 can also receive user selections from the first user interface 518 of FIG. 5. The communication unit 410 of FIG. 4 can detect the selections and the control unit 408 of FIG. 4 can send the detected selection to the select module 602. The first communication unit 516 of FIG. 5 can detect the selections and the first control unit 512 of FIG. 5 can send the detected selection to the select module 602. The second communication unit 536 of FIG. 5 can also detect the selections and the second control unit 534 of FIG. 5 can send the detected selection to the select module 602.

The context module 604 can receive the context boundary 208 of FIG. 2 and can receive the context furnishing 216 of FIG. 2 for generating the alert 206 of FIG. 2. The context module 604 can receive the layout and designation of the context boundary 208 for each outdoor area, building, room, or space in a building.

For example, the context module 604 can receive the selection of the context boundary 208 of FIG. 2, the restroom boundary 210 of FIG. 2, the bedroom boundary 212 of FIG. 2, or the open space boundary 224 of FIG. 2. The context module 604 can also receive the location and dimensions of the context boundary 208.

The context module 604 can also receive the selection of the context furnishing 216 of FIG. 2 in a similar way to the context boundary 208. For example, the context module 604 can receive the selection of the context furnishing 216, such as the bed 218 of FIG. 2, the dining set 220 of FIG. 2, or the bathtub 222 of FIG. 2.

The context module 604 can receive the location of the context furnishing 216 for display on the display interface 202 of FIG. 2. The context module 604 can receive user selections from the user interface 402. The context module 604 can also receive user selections from the first user interface 518. The context module 604 can detect the context furnishing 216 if the context furnishings 216 are appropriately equipped, such as with radio frequency identification (RFID). The detection and send of the context furnishing 216 can be performed in a similar or same manner as the selections for the select module 602.

The criteria module 606 can receive the boundary criteria 214 of FIG. 2 and can receive the furnishing criteria 226 of FIG. 2. The criteria module 606 can receive user selections from the user interface 402. The criteria module 606 can also receive user selections from the first user interface 518. As in the context module 604 for the context furnishing 216, the criteria module 606 can detect the boundary criteria 214 or the furnishing criteria 226. For example, the RFID can provide information for the boundary criteria 214 or the furnishing criteria 226. The criteria module 606 will be explained in greater detail below.

The monitoring module 608 can monitor the monitored person 204, the context boundary 208, the boundary criteria 214, the context furnishing 216, and the furnishing criteria 226. The monitoring module 608 can also determine the personal compliance 232 of FIG. 2 or the personal noncompliance 234 of FIG. 2 by monitoring the personal physical characteristic 228, the context boundary 208, the boundary criteria 214, the context furnishing 216, and the furnishing criteria 226 for generating the alert 206.

The monitoring module 608 can use the location unit 406 of FIG. 4, the communication unit 410 of FIG. 4, the control unit 408 of FIG. 4, or a combination thereof for monitoring. The monitoring module 608 can also use the location unit 520 of FIG. 5, the first communication unit 516 of FIG. 5, the first control unit 512 of FIG. 5, the second control unit 534 of FIG. 5, or the combination thereof for monitoring. The monitoring module 608 will be explained in greater detail below.

The navigation module 610 can generate and display routes to the monitored person 204. For example, if the first device 102 of FIG. 1 received the alert 206, the navigation module 610 can generate a route from the location of the first device 102 to the monitored person 204.

In emergency medical situations, paramedics and emergency medical technicians can immediately locate and arrive at the location of the monitored person 204. The navigation module 610 can display routes to the specific room or area where the monitored person 204 is located at instead of the general location or address. If the monitored person 204 is a child or prisoner, parents and authorities can locate and navigate to the room or area where the monitored person 204 is located.

The navigation module 610 can use the control unit 408, the communication unit 410, the location unit 406, or a combination thereof to generate routes to the monitored person 204. The navigation module 610 can use the display interface 202 to display the route. The navigation module 610 can also use the first control unit 512, the first communication unit 516, and the location unit 520 to generate routes to the monitored person 204. The navigation module 610 can use the first display interface 530 of FIG. 5 to display the route.

The navigation system 600 can be partitioned between the first device 502 of FIG. 5 and the second device 506 of FIG. 5. For example, the navigation system 600 can be partitioned between the first device 502 and the second device 506. The select module 602 can be partitioned on the first device 502 while the context module 604, the criteria module 606, the monitoring module 608, and the navigation module 610 can be partitioned on the second device 506. The navigation system 600 can also be implemented in the first device 102 of FIG. 4.

The select module 602 can be coupled to the context module 604. The context module 604 can be coupled to the criteria module 606. The criteria module 606 can be coupled to the monitoring module 608. The monitoring module 608 can be coupled to the navigation module 610.

The navigation system 600 describes the module functions or order as an example. The modules can be partitioned differently. For example, the select module 602, the context module 604, the criteria module 606, the monitoring module 608, and the navigation module 610 can be implemented as one module or with lesser number of modules. Each of the modules can operate individually and independently of the other modules.

Figure 7:
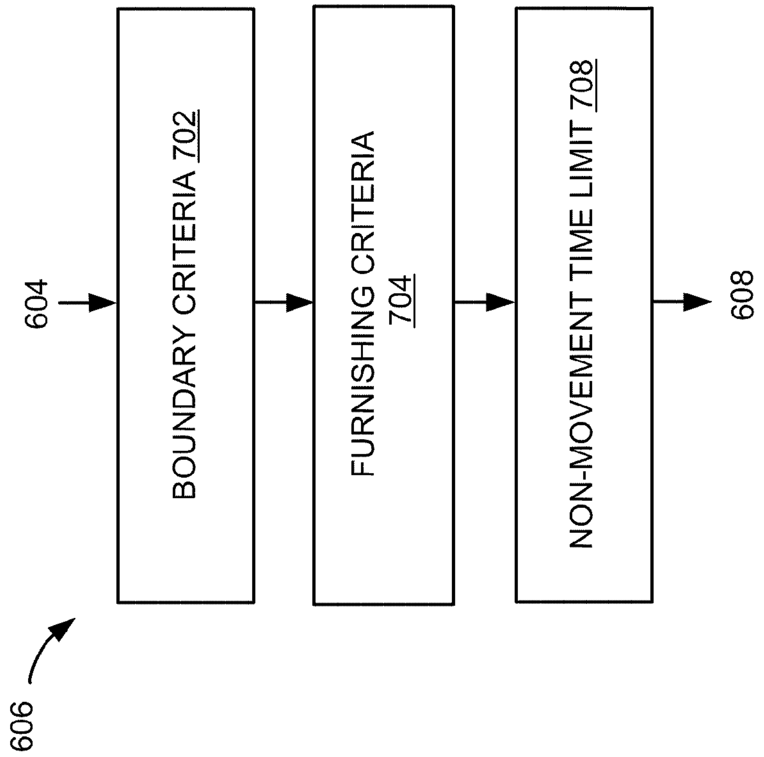
FIG. 7 is a detailed view of the criteria module.

Referring now to FIG. 7, therein is shown a detailed view of the criteria module 606 of FIG. 6. The criteria module 606 can receive information and criteria for generating the alert 206. The criteria module 606 can include a boundary criteria module 702, a furnishing criteria module 704, and a non-movement time limit module 708. The modules within the criteria module 606, as an example, can be indicated by a number and successively higher module numbers follow one another. Control flow can pass from one module to the next higher numbered module unless explicitly otherwise indicated.

The boundary criteria module 702 can receive the selection of the boundary criteria 214 of FIG. 2 such as the hazard 310 of FIG. 3. The boundary criteria module 702 can also display menus and request user-defined information. For example, the boundary criteria module 702 can request information regarding restrictions and time limits for the context boundary 208 for generating the alert 206.

The boundary criteria module 702 can receive the boundary criteria 214 from the user interface 402 of FIG. 4. The boundary criteria module 702 can also receive the boundary criteria 214 from the first user interface 518 of FIG. 5.

The boundary criteria module 702 can also detect the boundary criteria 214 as described in FIG. 6 for the criteria module 606. For example, the boundary criteria module 702 can also detect the open space boundary 224 of FIG. 2 by detecting space between the context furnishing 216 or by receiving the furnishing criteria 226 of FIG. 2.

The furnishing criteria module 704 can receive the selection of the furnishing criteria 226, such as the rest point 238 of FIG. 2 and the limited separation level 246 of FIG. 2. The furnishing criteria module 704 can also detect the furnishing criteria 226 regarding the context furnishing 216 in the context boundary 208. The furnishing criteria module 704 can also display menus and request user-defined information.

For example, the furnishing criteria module 704 can request information regarding restrictions and time limits for the context furnishing 216 of FIG. 2 to generate the alert 206. The furnishing criteria module 704 can receive the selection of the furnishing criteria 226 from the user interface 402. The furnishing criteria module 704 can also receive the selection of the furnishing criteria 226 from the first user interface 518.

The non-movement time limit module 708 can receive the non-movement time limit 236 of FIG. 2 for the boundary criteria 214 and the furnishing criteria 226. For example, the non-movement time limit module 708 can receive the selection of nine hours of the monitored person 204 being stationary in the bed 218 of FIG. 2 before generating the alert 206. The non-movement time limit module 708 can receive the selection of fifteen minutes for the open space boundary 224 of FIG. 2 before generating the alert 206.

The non-movement time limit module 708 can receive the non-movement time limit 236 from the user interface 402. The non-movement time limit module 708 can also receive the non-movement time limit 236 from the first user interface 518. The non-movement time limit module 708 can receive the non-movement time limit 236 with the communication unit 410, processed by the control unit 408, and stored in the storage unit 404 of FIG. 4. The non-movement time limit module 708 can also receive the non-movement time limit 236 with the first communication unit 516 or the second communication unit 536, processed by the first control unit 512 or the second control unit 534, and stored in the first storage unit 514 of FIG. 5 or the second storage unit 546 of FIG. 5.

The boundary criteria module 702 can be coupled to the furnishing criteria module 704. The furnishing criteria module 704 can be coupled to the non-movement time limit module 708.

For illustrative purposes, the modules of the criteria module 606 are described as discrete functional modules, although it is understood that these modules can have a different configuration. For example, the boundary criteria module 702, the furnishing criteria module 704, and the non-movement time limit module 708 can be implemented as one module or with lesser number of modules. Each of the modules can operate individually and independently of the other modules.

Figure 8:
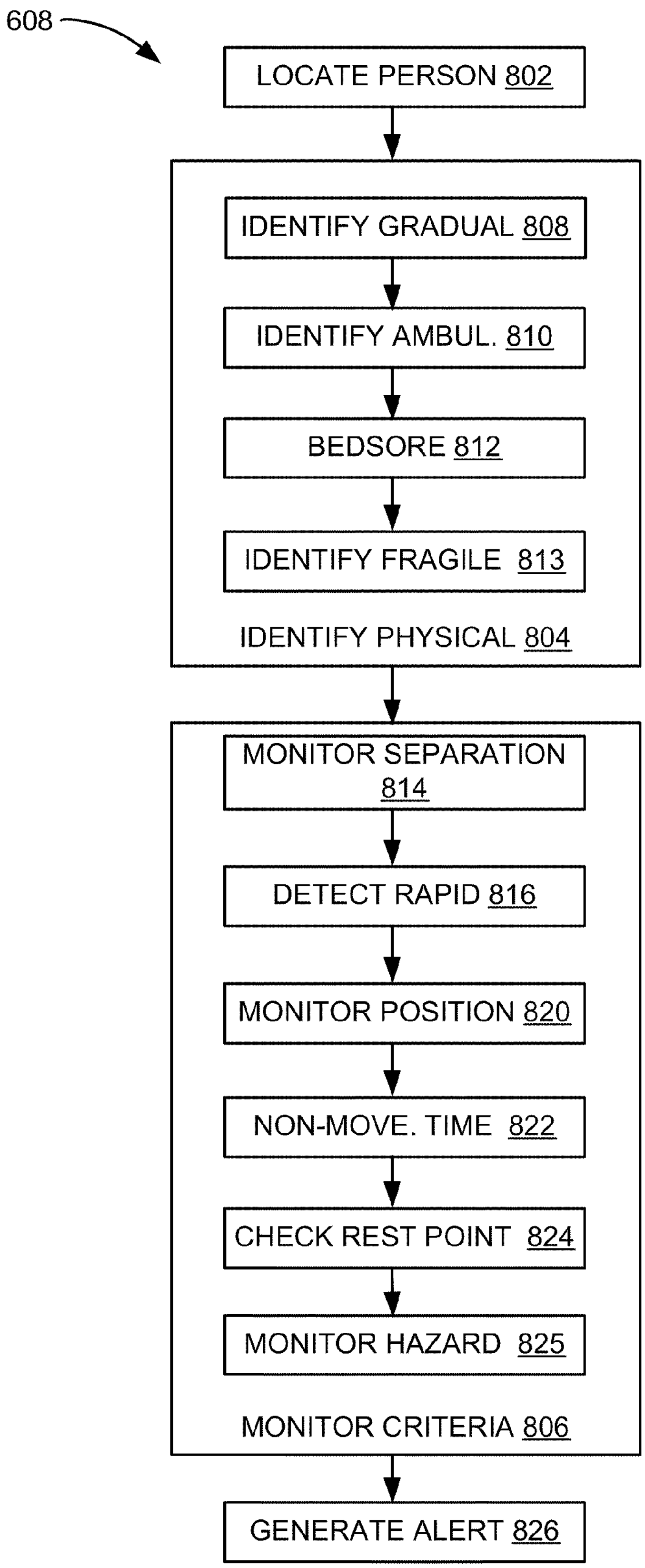
FIG. 8 is a detailed view of the monitoring module.

Referring now to FIG. 8, therein is shown a detailed view of the monitoring module 608 of FIG. 6. The monitoring module 608 can include a locate monitored person module 802, an identify physical module 804, a monitor criteria module 806, and a generate alert module 826. The modules within the monitoring module 608, as an example, can be indicated by a number and successively higher module numbers follow one another. Control flow can pass from one module to the next higher numbered module unless explicitly otherwise indicated.

For illustrative purposes, the modules of the monitoring module 608 are described as discrete functional modules, although it is understood that these modules can have a different configuration. For example, the identify physical module 804, the monitor criteria module 806, and the generate alert module 826 can be implemented as one module or with lesser number of modules. Each of the modules can operate individually and independently of the other modules.

The locate monitored person module 802 can locate and track the monitored person 204 of FIG. 2 to detect the personal location 244 of FIG. 2. The locate monitored person module 802 can use the location unit 406 to locate the monitored person 204 and the control unit 408 monitor the monitored person 204. The locate monitored person module 802 can also use to the location unit 520 to locate and the first control unit 512 or the second control unit 534 monitor the monitored person 204.

The identify physical module 804 can identify the personal physical characteristic 228 of the monitored person 204. The identify physical module 804 can include an identify gradual movement module 808, an identify ambulatory module 810, an identify bedsore position module 812, and an identify fragile physical level module 813.

The identify gradual movement module 808 can identify the gradual movement level 306 of FIG. 3 of the monitored person 204 for generating the alert 206 of FIG. 2. The identify gradual movement module 808 can track the current movements, movement trends, and average speed of the monitored person 204 to identify the gradual movement level 306.

For example, if the monitored person 204 is moving around in the wheelchair 248 of FIG. 2, factors like maneuverability and the average speed of the monitored person 204 can contribute to identifying the gradual movement level 306. The identify gradual movement module 808 can use the control unit 408 of FIG. 4 to identify the gradual movement level 306. The identify gradual movement module 808 can also use the first control unit 512 or the second control unit 534 to identify the gradual movement level 306.

The identify ambulatory module 810 can identify the limited ambulatory level 230 of FIG. 2 for generating the alert 206. The identify ambulatory module 810 can identify the limited ambulatory level 230 by analyzing the gradual movement level 306, the frequency of stops, rest periods, and the straightness of the walking path of the monitored person 204.

For example, a senior citizen may walk very slowly and with a crooked or staggered path. The senior citizen may also take frequency rest periods and rest on objects, such as pieces of furniture, as the senior citizen moves across the room. The identify ambulatory module 810 can identify these movement trends to identify the limited ambulatory level 230.

The limited ambulatory level 230 can be used with the non-movement time limit 236 of FIG. 2 and the rest point 238 of FIG. 2 to generate the alert 206. The identify ambulatory module 810 can use the control unit 408 to monitor the monitored person 204. The identify ambulatory module 810 can also use the first control unit 512 or the second control unit 534 to monitor the monitored person 204.

The identify bedsore position module 812 can identify the personal bedsore position 240 of FIG. 2 for generating the alert 206. The identify bedsore position module 812 can identify if the monitored person 204 has entered into a physical position that can cause bedsores. The identify bedsore position module 812 can use the control unit 408 to monitor the monitored person 204. The identify bedsore position module 812 can also use the first control unit 512 or the second control unit 534 to monitor the monitored person 204.

The identify fragile physical level module 813 can detect if the monitored person 204 has the fragile physical level 309 of FIG. 3. The identify fragile physical level module 813 can generate the fragile physical level 309 from medical records of the monitored person 204. For example, the medical records may indicate osteoporosis indicating fragility in the bones or the monitored person 204 requires a cane or crutches to be ambulatory.

The identify fragile physical level module 813 can also generate the fragile physical level 309 based on historical information of the monitored person 204. An example of the historical information includes recent falls in the context boundary 208.

The identify fragile physical level module 813 can use the control unit 408 to detect the fragile physical level 309. The identify fragile physical level module 813 can also use the first control unit 512 to detect the fragile physical level 309.

It has been discovered that the present invention provides a navigation system with context boundary monitoring mechanism for identifying a personal physical characteristic for monitoring boundary and furnishing criteria within the context boundary. The personal physical characteristic can be used to detect a person's physical actions and behavior, such as walking behavior for a specific location or interaction with furniture. When monitoring the personal physical characteristics, furnishing criteria, and boundary criteria, the navigation system can then monitor discrepancies or changes to the person's interactions, movement, or behavior that can suggest specific events, injuries or other problems associated with those locations have occurred.

For example, the navigation system can detect if a senior citizen, while traveling, has lost their cane or wheelchair by detecting a change in the personal gradual movement level. Further for example, the navigation system can detect a sudden change in the walking speed of a monitored person while in a stairway. The alert generated from this event can suggest that the monitored person has fallen down the stairs.

The monitor criteria module 806 can monitor the boundary criteria 214 and the furnishing criteria 226 of FIG. 2 for generating the alert 206. The monitor criteria module 806 can access criteria information and the personal physical characteristic 228 to determine the personal compliance 232 or the personal noncompliance 234 of FIG. 2. The monitor criteria module 806 can include a monitor separation module 814, a detect rapid movement module 816, a monitor position module 820, a monitor non-movement time limit module 822, a check rest point module 824, and a monitor hazard module 825.

The monitor criteria module 806 can instruct the generate alert module 826 to generate the alert 206. For example, if the monitor criteria module 806 detects the personal noncompliance 234, the monitor criteria module 806 can instruct the generate alert module 826 to generate the alert 206. The generate alert module 826 can also generate the alert 206 based on the personal compliance 232 of FIG. 2. The alert 206 based on the personal compliance 232 can provide information that the monitored person 204 has completed an expected action or that the monitored person 204 has passed a user-defined safety check.

The monitor separation module 814 can monitor the limited separation level 246, the personal location 244, and the furnishing criteria 226 for generating the alert 206. For example, if the monitor separation module 814 detects that the personal location 244 is beyond the limited separation level 246 from the wheelchair 248, then the alert 206 can be generated. This situation represents that the monitored person 204 has been separated from the context furnishing 216, such as the wheelchair 248.

The monitor separation module 814 can also check the limited ambulatory level 230 before generating the alert 206. If the monitored person 204 has trouble walking and is separated from the context furnishing 216, then the alert 206 can be generated. If the monitored person 204 does not have trouble walking, then the generating of the alert 206 can be disabled in this situation. The monitor separation module 814 can use the control unit 408 to monitor the monitored person 204. The monitor separation module 814 can also use the first control unit 512 or the second control unit 534 to monitor the monitored person 204.

The detect rapid movement module 816 can detect if the personal rapid movement 312 of FIG. 3 has occurred for generating the alert 206. The detect rapid movement module 816 can monitor the gradual movement level 306 and monitor for the personal rapid movement 312. The detect rapid movement module 816 can detect sudden accelerations in movement, a sudden elevation change, the distance in which the movement occurred, and location of the movement to detect the personal rapid movement 312.

The personal rapid movement 312 can suggest that the monitored person 204 has fallen or was injured for generating the alert 206. The detect rapid movement module 816 can use the control unit 408 to detect the personal rapid movement 312. The detect rapid movement module 816 can also use the first control unit 512 or the second control unit 534 to detect the personal rapid movement 312.

It has been also discovered that the present invention provides a navigation system providing improved monitoring of persons to improve public safety, to improve rendering of health services, and lowering cost. The ability of the navigation system allows people to care for and monitored people with less effort and reduction of headcount required for monitoring people. Assistance and more expedient care can be provided by alert reducing the human oversight to situations that may need to be checked from time to time or in situations that are likely problematic.

It has been further discovered that the present invention provides a navigation system with context boundary monitoring mechanism for monitoring a limited separation level and a personal rapid movement. The navigation system can detect discrepancies to the personal physical characteristics, such as a personal rapid movement, and compare it to the context boundary where the discrepancy occurred. With this information, the navigation system can generate an alert of a possible problem such as a fall, unexpected injury, or event. For example, if the personal rapid movement occurred near a stairway, the alert can indicate that the monitored person may have fallen down the stairs.

The monitor position module 820 can monitor the personal bedsore position 240 for generating the alert 206. For example, the personal bedsore position 240 can be determined by multiple sensors (not shown) on or proximate to the monitored person 204. The relative locations, such as height, of the multiple sensors along with time duration at that position can indicate the personal bedsore position 240.

The non-movement time limit 236 of FIG. 2 can be used to monitor the monitored person 204 in the bed 218 of FIG. 2 to prevent bedsores. If the monitor position module 820 detects the personal bedsore position 240 and that the monitored person 204 has been stationary for a certain time, the monitor position module 820 can begin the non-movement time limit 236 for this situation.

If the monitor position module 820 continues to detect the personal bedsore position 240 exceeding the non-movement time limit 236, then the alert 206 can be generated. The monitor position module 820 can use the control unit 408 to monitor the personal bedsore position 240. The monitor position module 820 can also use the first control unit 512 or the second control unit 534 to monitor the personal bedsore position 240.

The monitor non-movement time limit module 822 can monitor the non-movement time limit 236 for the other examples of the boundary criteria 214 and the furnishing criteria 226. The monitor non-movement time limit module 822 can monitor when the monitored person 204 remains stationary beyond the non-movement time limit 236. The monitor non-movement time limit module 822 can also adjust the non-movement time limit 236 based on the personal physical characteristics 228.

For example, if the monitored person 204 is in the open space boundary 224 of FIG. 2, the monitor non-movement time limit module 822 can shorten the non-movement time limit 236 if the monitored person 204 has a low level of the limited ambulatory level 230. This increases the sensitivity of detecting a person who cannot walk too much to generate the alert 206 earlier than someone who has no problem walking.

The open space boundary 224 will not have any of the context furnishing 216 that can provide the rest point 238 of FIG. 2 for the monitored person 204 to rest on. For example, if a senior citizen with a low level of the limited ambulatory level 230 remains stationary beyond the non-movement time limit 236, a problem may have occurred such as a fall or injury.

The monitor non-movement time limit module 822 can use the control unit 408 to monitor the non-movement time limit 236. The monitor non-movement time limit module 822 can also use the first control unit 512 or the second control unit 534 to monitor the non-movement time limit 236.

The check rest point module 824 can modify the non-movement time limit 236 if the check rest point module 824 detects the rest point 238. If the monitored person 204 is at the context furnishing 216 that has the furnishing criteria 226 as the rest point 238, the check rest point module 824 can modify the non-movement time limit 236 to be for a longer time period.

For example, if the non-movement time limit 236 for the context boundary 208 is selected for fifteen minutes, the check rest point module 824 can disable or modify the alert 206 if the monitored person 204 is at the rest point 238. Another example is the check rest point module 824 can increase the non-movement time limit 236 while the monitored person 204 is at the rest point 238.

The check rest point module 824 can use the control unit 408 to monitor the rest point 238 The check rest point module 824 can also use the first control unit 512 or the second control unit 534 to monitor the rest point 238.

The monitor hazard module 825 can monitor the monitored person 204 with the fragile physical level 309 proximity to the hazard 310 of FIG. 3 for generating the alert 206. For example, the monitor hazard module 825 can detect if the personal location 244 is proximate to the hazard 310 for the monitored person 204 with the fragile physical level 309. If the monitor hazard module 825 detects that the monitored person 204 is near an area that has the hazard 310 as the boundary criteria 214, the alert 206 can be generated.

The monitor hazard module 825 can use the control unit 408 to monitor the hazard 310. The monitor hazard module 825 can also use the first control unit 512 or the second control unit 534 to monitor the hazard 310.

It has been yet further been discovered that the present invention provides a navigation system with context boundary monitoring mechanism for monitoring boundary criteria and furnishing criteria. The criteria can include a non-movement time limit, a rest point, and a hazard. The navigation system can monitor the context of a boundary including the rules and the personal physical characteristics that correspond to specific rooms or specific monitored areas.

For example, the navigation system can modify the non-movement time limit based on the personal physical characteristics and the personal location in relationship to the context boundary such as the open space boundary. The alerts can be individualized to each personal physical characteristics so elderly people will have different rules than other adults or children. For elderly, the non-movement time limit can provide alerts to suggest that the person has been injured, to prevent bedsores, and to suggest that might have passed away.

The navigation system can also detect context furnishings that are rest points. By combining the personal physical characteristics with boundary and furnishing criteria, the navigation system can generate accurate and specific alerts. These accurate and specific alerts can help people get immediate attention or provide useful reminders.

It has been yet further found that the context boundary, the context furnishing, the boundary criteria, the furnishing criteria, and the personal physical characteristic can all be monitored to provide many new tools in keeping loved ones or monitored people secure. The context boundary and the context furnishing allow precise detail in mapping areas and more accuracy in navigation.

The physical transformation of the alert 206, the boundary criteria 214, the furnishing criteria 226, the personal physical characteristic 228, the personal bedsore position 240, and the hazard 310 results in movement in the physical world, such as people using the first device 102 or vehicles, based on the operation of the navigation system 600. As the movement in the physical world occurs, the movement itself creates additional information that is converted back to the alert 206, the boundary criteria 214, the furnishing criteria 226, the personal physical characteristic 228, the personal bedsore position 240, and the hazard 310 for the continued operation of the navigation system 600 and to continue the movement in the physical world.

Thus, it has been discovered that the navigation system of the present invention furnishes important and heretofore unknown and unavailable solutions, capabilities, and functional aspects for a navigation system for monitoring people and objects.

Figure 9:
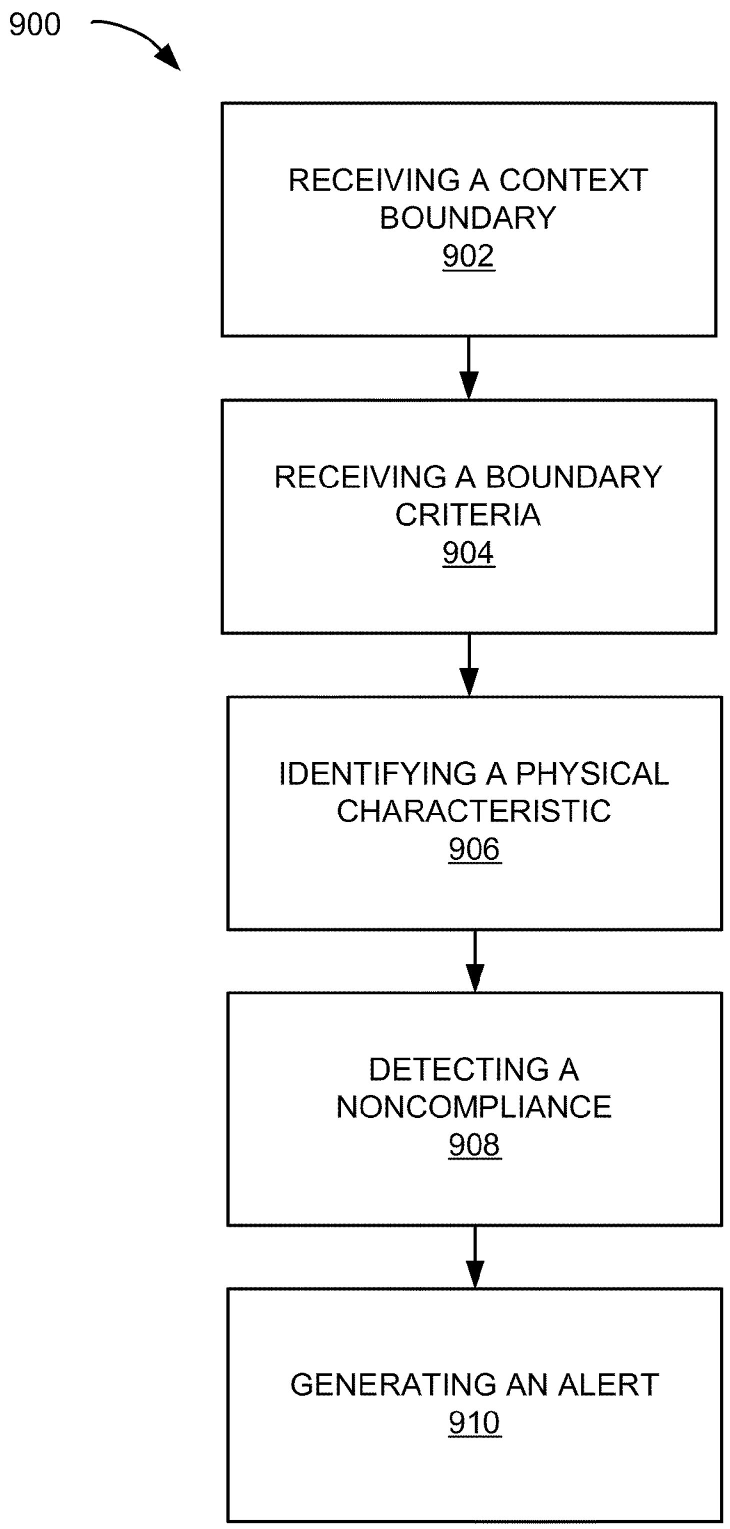
FIG. 9 is a flow chart of a method of operation of a navigation system in a further embodiment of the present invention.

Referring now to FIG. 9, therein is shown a flow chart of a method 900 of operation of a navigation system in a further embodiment of the present invention. The method 900 includes: receiving a context boundary in a block 902; receiving a boundary criteria for the context boundary in a block 904; identifying a personal physical characteristic for monitoring a monitored person in a block 906, detecting a personal noncompliance to the boundary criteria based on a discrepancy of the personal physical characteristic in a block 908; and generating an alert based on the personal noncompliance for displaying on a device in a block 910.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of the present invention is that it valuably supports and services the historical trend of reducing costs, simplifying systems, and increasing performance. These and other valuable aspects of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A method of operation of a navigation system comprising:

receiving a context boundary;

receiving a boundary criteria for the context boundary;

identifying a personal physical characteristic for monitoring a monitored person;

detecting a personal noncompliance to the boundary criteria based on a discrepancy of the personal physical characteristic; and generating an alert based on the personal noncompliance for displaying on a device.

2. The method as claimed in claim 1 further comprising:

receiving a context furnishing;

receiving a furnishing criteria for the context furnishing; and detecting the personal noncompliance to the furnishing criteria based on the discrepancy with the personal physical characteristic.

3. The method as claimed in claim 1 wherein:

receiving the context boundary includes receiving an open space boundary;

receiving the boundary criteria includes receiving a non-movement time limit for the open space boundary;

identifying the personal physical characteristic includes identifying a limited ambulatory level; and detecting the personal noncompliance includes detecting the limited ambulatory level within the open space boundary and exceeding the non-movement time limit.

4. The method as claimed in claim 1 further comprising:

receiving a context furnishing;

detecting a personal location; and wherein:

receiving the boundary criteria includes receiving a limited separation level from the context furnishing;

identifying the personal physical characteristic includes identifying a limited ambulatory level; and detecting the personal noncompliance includes detecting the personal location separated beyond the limited separation level.

5. The method as claimed in claim 1 further comprising:

detecting a personal location; and wherein:

receiving the boundary criteria includes receiving a hazard;

identifying the personal physical characteristic includes identifying a fragile physical level; and detecting the personal noncompliance includes detecting the personal location proximate to the hazard that is incompatible to the fragile physical level.

6. A method of operation of a navigation system comprising:

receiving a context boundary and a context furnishing;

receiving a boundary criteria and a furnishing criteria;

identifying a personal physical characteristic for monitoring a monitored person;

detecting a personal noncompliance to the boundary criteria and the furnishing criteria based on a discrepancy with the personal physical characteristic; and generating an alert based on the personal noncompliance for displaying on a device.

7. The method as claimed in claim 6 further comprising:

detecting a personal location; and wherein:

receiving the boundary criteria includes receiving a non-movement time limit;

identifying the personal physical characteristic includes identifying a limited ambulatory level;

receiving the furnishing criteria includes receiving a rest point; and detecting the personal noncompliance includes detecting the personal location away from the rest point and exceeding the non-movement time limit and the limited ambulatory level.

8. The method as claimed in claim 6 wherein:

receiving the boundary criteria includes receiving a non-movement time limit;

identifying the personal physical characteristic includes identifying a limited ambulatory level;

receiving the furnishing criteria includes receiving a rest point; and further comprising:

detecting a personal location proximate to the rest point; and modifying the non-movement time limit based on the limited ambulatory level and the rest point.

9. The method as claimed in claim 6 further comprising:

detecting a personal rapid movement; and wherein:

identifying the personal physical characteristic includes identifying a gradual movement level; and detecting the personal noncompliance includes detecting the personal rapid movement that is incompatible with the gradual movement level.

10. The method as claimed in claim 6 wherein:

receiving the context furnishing includes identifying a bed;

receiving the furnishing criteria includes receiving a non-movement time limit for the bed;

identifying the personal physical characteristic includes identifying a personal bedsore position; and detecting the personal noncompliance to the furnishing criteria includes detecting the personal bedsore position on the bed and exceeding the non-movement time limit.

11. A navigation system comprising:

a context module for receiving a context boundary;

a criteria module, coupled to the context module, for receiving a boundary criteria for the context boundary;

an identify physical module, coupled to the criteria module, for identifying a personal physical characteristic for monitoring a monitored person;

a monitor criteria module, coupled to the identify physical module, for detecting a personal noncompliance to the boundary criteria based on a discrepancy of the personal physical characteristic; and a generate alert module, coupled to the monitor criteria module, for generating an alert based on the personal noncompliance for displaying on a device.

12. The system as claimed in claim 11 wherein:

the context module is for receiving a context furnishing;

the criteria module is for receiving a furnishing criteria for the context furnishing; and the monitor criteria module is for detecting the personal noncompliance to the furnishing criteria based on the discrepancy of the personal physical characteristic.

13. The system as claimed in claim 11 wherein:

the context module is for receiving an open space boundary;

the criteria module is for receiving a non-movement time limit for the open space boundary; and further comprising:

an identify ambulatory module, coupled to the criteria module, for identifying a limited ambulatory level; and a non-movement time limit module, coupled to the identify ambulatory module, for detecting the limited ambulatory level within the open space boundary and exceeding the non-movement time limit.

14. The system as claimed in claim 11 wherein:

the context module is for receiving a context furnishing; and further comprising:

a locate monitored person module, coupled to the context module, for detecting a personal location;

a furnishing criteria module, coupled to the locate person module, for receiving a limited separation level from the context furnishing;

an identify ambulatory module, coupled to the furnishing criteria module, for identifying a limited ambulatory level; and a monitor separation module, coupled to the identify ambulatory module, for detecting the personal location separated beyond the limited separation level.

15. The system as claimed in claim 11 wherein:

the criteria module is for receiving a hazard;

further comprising:

a locate monitored person module, coupled to the criteria module, for detecting a personal location;

an identify fragile physical level module, coupled to the locate monitored person module, for identifying the fragile physical level; and a monitor hazard module, coupled to the identify fragile physical level module, for detecting the personal location proximate to the hazard that is incompatible to the fragile physical level.

16. The system as claimed in claim 11 wherein:

the context module is for receiving the context boundary and a context furnishing;

the criteria module is for receiving the boundary criteria and a furnishing criteria; and the monitor criteria module, coupled to the criteria module, is for detecting the personal noncompliance to the boundary criteria and the furnishing criteria based on the discrepancy of the personal physical characteristic.

17. The system as claimed in claim 16 further comprising:

a locate monitored person module for detecting a personal location;

a non-movement time limit module, coupled to the locate monitored person module, for receiving a non-movement time limit;

an identify ambulatory module, coupled to the non-movement time limit module, for identifying a limited ambulatory level;

a furnishing criteria module, coupled to the identify ambulatory module, for receiving a rest point; and wherein:

the monitor criteria module, coupled to the furnishing criteria module, is for detecting the personal location away from the rest point and exceeding the non-movement time limit and the limited ambulatory level.

18. The system as claimed in claim 16 wherein:

the criteria module is for receiving a rest point; and further comprising;

a non-movement time limit module, coupled to the criteria module for receiving a non-movement time limit;

an identify ambulatory module, coupled to the non-movement time limit module, for identifying a limited ambulatory level;

a locate monitored person module, coupled to the identify ambulatory module, for detecting a personal location proximate to the rest point; and a check rest point module, coupled to the locate monitored person module, for modifying the non-movement time limit based on the limited ambulatory level and the rest point.

19. The system as claimed in claim 16 further comprising:

a locate monitored person module for detecting a personal rapid movement;

an identify gradual movement module, coupled to the locate monitored person module, for identifying a gradual movement level; and a detect rapid movement module, coupled to the identify gradual movement module, for detecting the personal rapid movement that is incompatible with the gradual movement level.

20. The system as claimed in claim 16 wherein:

the monitor criteria module is for identifying a bed; and further comprising:

a furnishing criteria module, coupled to the monitor criteria module, for receiving a non-movement time limit for the bed;

an identify bedsore position module, coupled to the furnishing criteria module, for identifying a personal bedsore position; and a monitor position module, coupled to the identify bedsore position module, for detecting the personal bedsore position on the bed and exceeding the non-movement time limit.

* * * * *